US007050877B2

(12) United States Patent
Iseki et al.

(10) Patent No.: US 7,050,877 B2
(45) Date of Patent: May 23, 2006

(54) METHOD FOR MODELING AN IMPLANT AND AN IMPLANT MANUFACTURED BY THE METHOD

(75) Inventors: Hiroshi Iseki, 7-33, Nishinippori 3-chome, Arakawa-ku, Tokyo (JP); Keita Abe, Tokyo (JP); Yoshiyuki Ogawara, Tochigi (JP)

(73) Assignees: PENTAX Corporation, Tokyo (JP); Hiroshi Iseki, Tokyo (JP)

( * ) Notice: Subject to any disclaimer, the term of this patent is extended or adjusted under 35 U.S.C. 154(b) by 231 days.

(21) Appl. No.: 10/626,533

(22) Filed: Jul. 25, 2003

(65) Prior Publication Data

US 2004/0138591 A1 Jul. 15, 2004

(30) Foreign Application Priority Data

Jul. 26, 2002 (JP) ............................. 2002-218153

(51) Int. Cl.
*G06F 19/00* (2006.01)

(52) U.S. Cl. ..................... 700/118; 700/97; 623/17.19; 623/901

(58) Field of Classification Search ................. 700/95, 700/97, 118, 182; 623/17.19, 901, 11.11, 623/16.11; 128/897, 898
See application file for complete search history.

(56) References Cited

U.S. PATENT DOCUMENTS

| 4,436,684 | A | * | 3/1984 | White | 264/138 |
| 4,873,707 | A | * | 10/1989 | Robertson | 378/18 |
| 4,976,737 | A | * | 12/1990 | Leake | 128/898 |
| 5,503,164 | A | * | 4/1996 | Friedman | 128/898 |
| 5,768,134 | A | * | 6/1998 | Swaelens et al. | 700/121 |
| 6,083,264 | A | * | 7/2000 | Wood et al. | 623/23.56 |
| 6,112,109 | A | * | 8/2000 | D'Urso | 600/407 |
| 6,254,639 | B1 | * | 7/2001 | Peckitt | 623/11.11 |
| 6,540,784 | B1 | * | 4/2003 | Barlow et al. | 623/16.11 |
| 6,775,352 | B1 | * | 8/2004 | Toth et al. | 378/108 |
| 6,786,930 | B1 | * | 9/2004 | Biscup | 623/16.11 |

FOREIGN PATENT DOCUMENTS

JP 5-192362 8/1993

* cited by examiner

*Primary Examiner*—Leo Picard
*Assistant Examiner*—Alexander Kosowski
(74) *Attorney, Agent, or Firm*—Greenblum & Bernstein, P.L.C.

(57) ABSTRACT

A method for modeling an implant to be applied to a defect of a bone comprises the steps of obtaining a plurality of tomographic image data of the bone based on measurement data by MRI, producing three-dimensional image data of the bone based on the plurality of tomographic image data, and estimating a shape of a missing born that was previously present or should have been present in the defect of the bone to obtain three-dimensional data of the implant. The estimating step comprises the steps of estimating a provisional shape of the implant which has a contour conformable with the shape of a contour of periphery of the side walls of the defect at the distal surface of the bone and has a predetermined thickness; and deleting data of portions of the provisional shape of the implant that overlap the bone from the data of the provisional shape of the implant so that the three-dimensional data of the implant has an outer peripheral shape that is conformable with the shape of the side walls of the defect.

18 Claims, 9 Drawing Sheets

METHOD FOR MODELING AN IMPLANT AND AN IMPLANT MANUFACTURED BY THE METHOD

BACKAGROUND OF THE INVENTION

1. Field of the Invention

This invention relates to a method for modeling an implant and an implant manufactured by the method.

2. Description of the Prior Art

In the case where a part of a bone such as a cranium bone, a facial bone or a maxillofacial bone is lost due to an accident such as a traffic accident or the like, an implant made of an artificial material is embedded and fixed to a defect of the bone (that is, bone defect reconstruction is carried out). Such a bone defect reconstruction is also carried out when a part of such a bone is removed due to a surgical operation for a bone tumor or the like.

In the bone defect reconstruction, the material of the implant and its shape are important factors.

As for a material of an implant, ceramics or the like are widely used because of its excellent biocompatibility.

On the other hand, conventionally, the shape of an implant is determined as follows.

First, a plurality of different cross-sectional images of a bone having a defect are taken with CT. Next, a wood plate is processed into a shape corresponding to each CT image of the bone. Then, processed plates are stacked and they are bonded together to produce a bone model having the shape corresponding to the bone. Then, a clay or the like is packed into a part of the defect in the bone model to obtain a clay mock-up having the shape corresponding to the defect of the bone. Thus obtained mock-up is formed with steps corresponding to the thickness of each plate on the outer periphery thereof.

Then, the mock-up is molded with a resin material to obtain a female mold, and then using the female mold a male mold made of a resin material is formed. Thereafter, the outer periphery of the male mold is shaved using a cutter to form a smooth outer peripheral surface having no steps, and it is employed as a shape of the implant (a shape of a missing bone that should have been present in the defect of the bone).

However, when the shape of the implant is modeled according to the above method, there are problems such as follows.

Namely, in the method mentioned above, the model is formed using a plurality of plates. Each of such plates has a relatively large thickness. Thus, it is difficult to accurately form a model of the bone having the defect.

Further, in the method mentioned above, the outer periphery of the male mold is shaved using a cutter or the like to form a smooth outer peripheral surface, while no consideration is paid to the shape of the side walls of the defect of the bone. Therefore, there is a case that the implant that is modeled by this method has poor conformity with the shape of the defect of the bone.

In the conventional method, it may be possible to improve conformability of the model by making each plate thinner, but there is a limit in this approach, thus it is difficult to obtain satisfactory shape conformability. Further, when the thickness of the plate is made thinner, it takes a relatively long time to manufacture a mock-up. Therefore, this approach can not be applied for the case where it is not possible to leave a patient with a bone defect for a long time, thus this approach is not practical.

Furthermore, in the case where the shape of an implant is determined as described above, it is necessary to take a plurality of CT scanning images along a plurality of different cross sections of a bone having a defect. However, since CT scanning images are taken using X-rays, a patient is necessarily exposed to predetermined doses of X-ray radiations. Further, in order to form a model having a more accurate shape, it is necessary to take many more CT scanning images, thus leading to a problem in that a patient will be exposed to massive doses of X-ray radiations.

SUMMARY OF THE INVENTION

It is therefore an object of the present invention to provide a method for modeling an implant having excellent shape-conformability with a defect of a bone and to provide an implant manufactured by the method.

In order to achieve the object, the present invention is directed to a method for modeling an implant to be applied to a defect of a bone which is defined by side walls. The method comprises the steps of: obtaining a plurality of tomographic image data of the bone based on measurement data by MRI; producing three-dimensional image data of the bone based on the plurality of tomographic image data; and estimating a shape of a missing born that was previously present or should have been present in the defect of the bone to obtain three-dimensional data of the implant, wherein the three-dimensional data of the implant is modeled such that at least a part of the outer periphery of the implant is conformable with the shape of the side walls of the defect of the bone.

According to the method described above, it is possible to provide an implant having excellent shape-conformability with a defect of a bone.

In this method, it is preferred that the tomographic image data is obtained by obtaining threshold value inverting data by inverting a threshold value of the measurement data by MRI, and then extracting a born region from the threshold value inverting data.

This makes it possible to further improve the shape-conformability with the defect of the bone.

Further, in the method described above, it is also preferred that the estimating step comprises the steps of: estimating a provisional shape of the implant which has a contour conformable with the shape of a contour of periphery of the side walls of the defect at the distal surface of the bone and has a predetermined thickness; and deleting data of portions of the provisional shape of the implant that overlap the bone from the data of the provisional shape of the implant so that the three-dimensional data of the implant has an outer peripheral shape that is conformable with the shape of the side walls of the defect.

This also makes it possible to further improve the shape-conformability with the defect of the bone.

Further, the estimating step may comprise the steps of: producing data of a contour of a distal surface of the implant so that the contour is conformable with the shape of a contour of periphery of the side walls at the distal surface of the bone; estimating a provisional shape of the implant which has a predetermined thickness and has a substantially predetermined shape in the thickness direction thereof using the data of the contour of the distal surface of the implant; and deleting data of portions of the provisional shape that overlap the bone from the data of the provisional shape of the implant so that the three-dimensional data of the implant has an outer peripheral shape that is conformable with the shape of the side walls of the defect.

This also makes it possible to further improve the shape-conformability with the defect of the bone.

Furthermore, the estimating step may comprise the steps of: producing data of a contour of a distal surface of the implant so that the contour is conformable with the shape of a contour of periphery of the side walls at the distal surface of the bone; estimating a provisional shape of the implant which has a predetermined thickness and has a substantially predetermined shape in the thickness direction thereof using the data of the contour of the distal surface of the implant; and correcting the data of the provisional shape so that the three-dimensional data of the implant has an outer peripheral shape that is conformable with the shape of the side walls of the defect by comparing the estimated data of the provisional shape of the implant with the data of the side walls of the three-dimensional image data.

This also makes it possible to further improve the shape-conformability with the defect of the bone.

In the present invention, it is also preferred that when the implant is applied to the defect of the bone, the distal surface of the implant forms a continuous surface with the distal surface of the bone.

This also makes it possible to further improve the shape-conformability with the defect of the bone.

Further, it is also preferred that the bone substantially has plane symmetry, in which the estimation of the shape of the missing bone is carried out utilizing data of a portion in the three-dimensional image data which is plane-symmetrical with the defect in the three-dimensional image data.

This also makes it possible to further improve the shape-conformability with the defect of the bone.

In a preferred embodiment, the bone is a cranium bone.

Further, in the method described above, it is preferred that the plurality of tomographic images for producing the three-dimensional image data are taken with a predetermined slice interval between the adjacent images, in which the slice interval is in the range of 0.1 to 5 mm.

Another aspect of the present invention is directed to an implant which is manufactured based on a model prepared in accordance with the modeling method as defined in any one of claims 1 to 9.

The implant has especially excellent shape-conformability with the defect of the bone.

Further, it is preferred that the implant is manufactured through a manufacturing process which comprises: a first step for forming a layer made of material powder; and a second step for hardening the material powder by making at least a part of the layer contact with a reaction liquid, wherein the first step and the second step are carried out repeatedly to obtain a laminate comprised of a plurality of the layers, thereby manufacturing an implant having a shape corresponding to the three-dimensional data of the implant provided by the modeling method.

By manufacturing the implant in this way, it is possible to have excellent dimensional accuracy even if the implant has a complicated shape.

In this case, it is preferred that the implant has a porosity of 10 to 90 vol %.

This makes it possible to improve biocompatibility with a living body.

These and other objects, structures and results of the present invention will be apparent more clearly when the following detailed description of the preferred embodiments is considered taken in conjunction with the accompanying drawings.

DETAILED DESCRIPTION OF THE PREFERRED EMBODIMENTS

Hereinbelow, based on the accompanying drawings, a detailed description will be made with regard to a preferred embodiment of a method for modeling an implant and an implant manufactured by the method according to the present invention.

Figure 1:
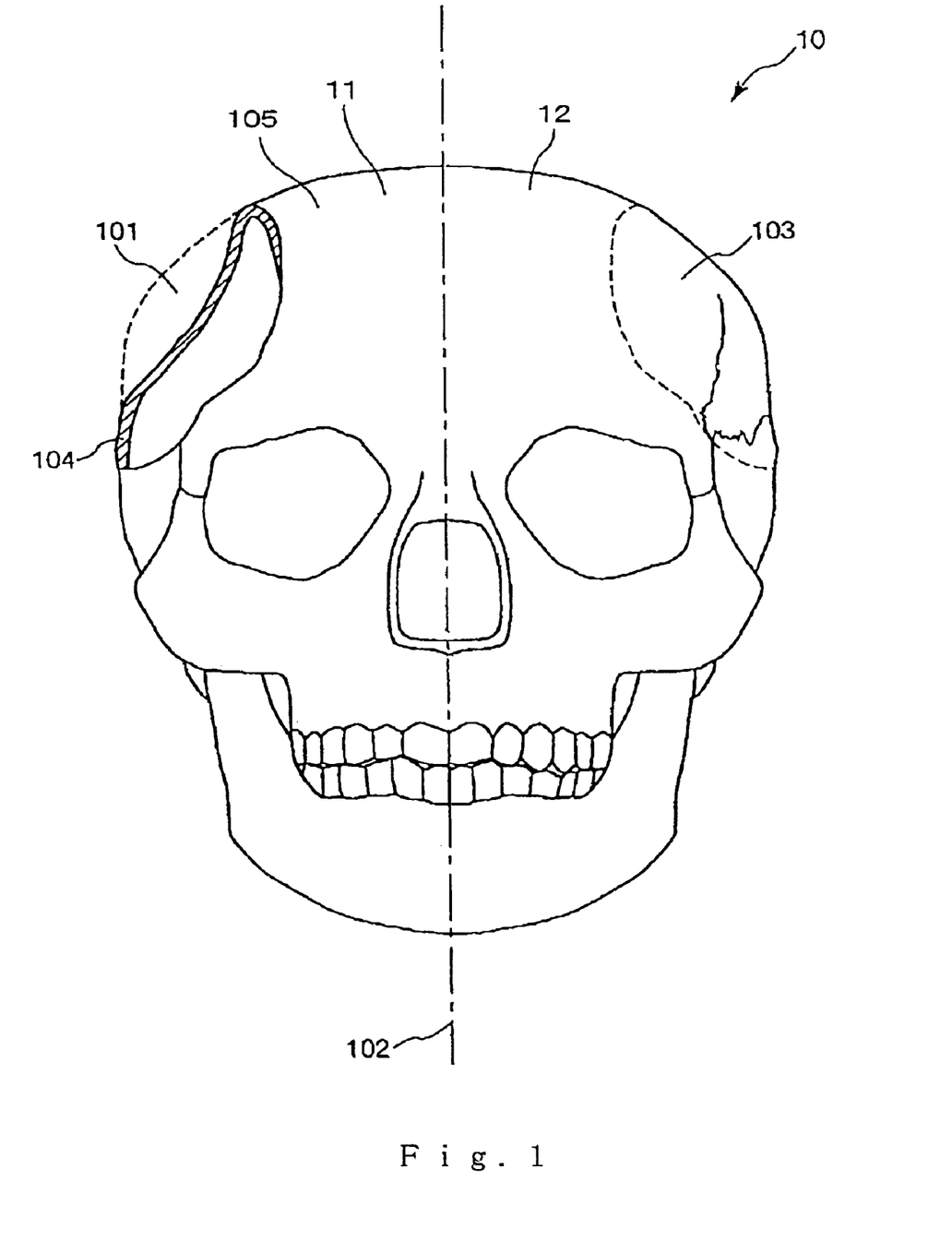
FIG. 1 is an illustration of three-dimensional data of a bone produced based on a plurality of tomographic image data.
Figure 2:
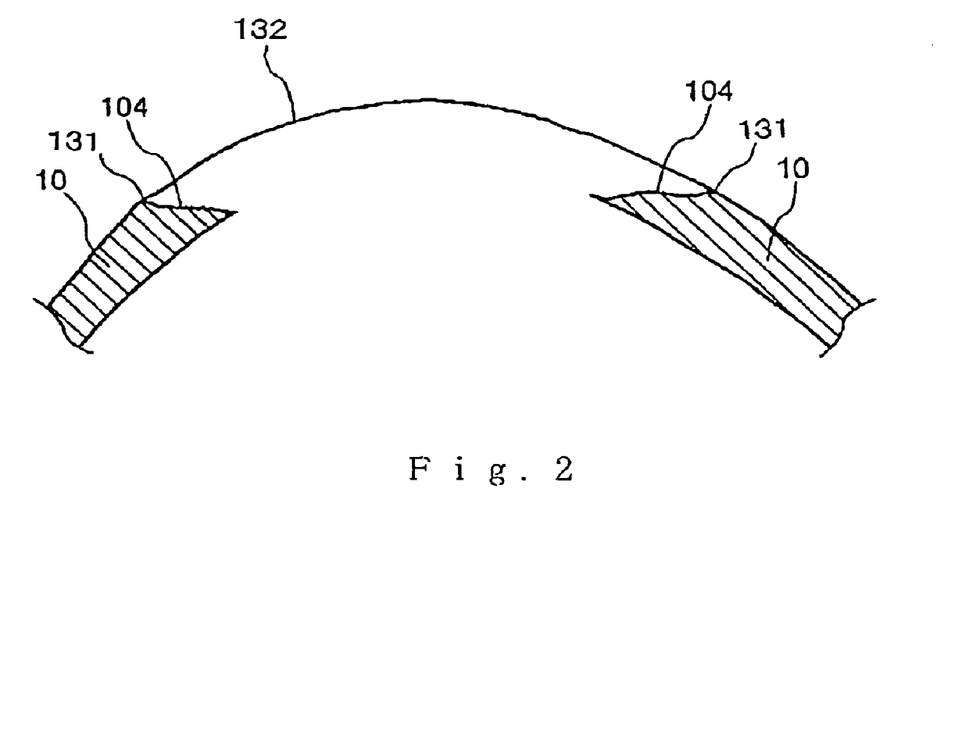
FIG. 2 is an illustration which shows a state that contour data of the distal surface of a missing bone that should have been present in the defect is superposed on the data of the defect of the bone.
Figure 3:
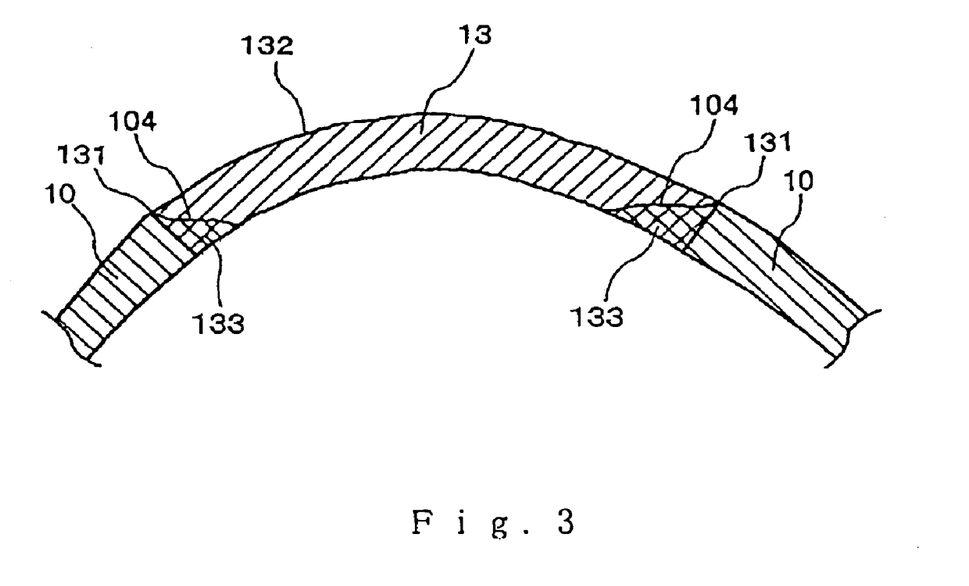
FIG. 3 is an illustration which shows a state that data of the missing bone having a predetermined thickness is superposed on the data of the defect of the bone.
Figure 4:
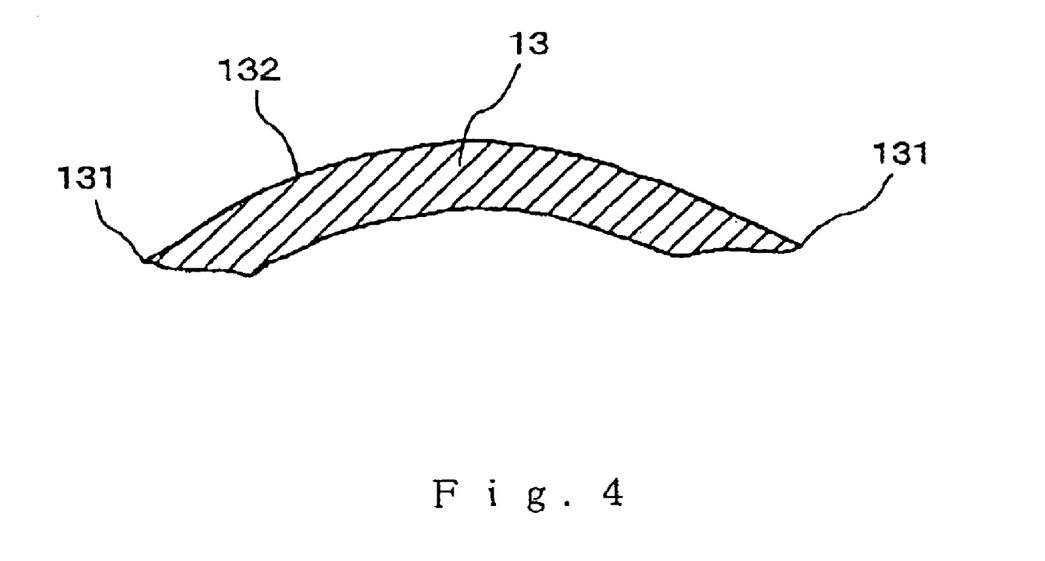
FIG. 4 is an illustration which shows data of the missing bone which has been processed so as to conform with the inclined surfaces of the side walls of the defect of the bone.

FIG. 1 is an illustration of three-dimensional data of a bone produced based on a plurality of tomographic image data, FIG. 2 is an illustration which shows a state that contour data of the distal surface of a missing bone that should have been present in the defect is superposed on the data of the defect of the bone, FIG. 3 is an illustration which shows a state that data of the missing bone having a predetermined thickness is superposed on the data of the defect of the bone, and FIG. 4 is an illustration which shows data of the missing bone which has been processed so as to conform with the inclined surfaces the side walls of the defect of the bone. In connection with these drawings, it is to be noted that in FIGS. 2 to 4, the upper side is a distal surface (outer surface) side of the bone in three-dimensional data and the lower side is a proximal surface (inner surface) side of the bone in the three-dimensional data.

In the present invention, a bone to which an implant is applied is not limited to a specific bone, but it is preferred that the implant is applied to a bone having plane symmetry. This is because if a bone has plane symmetry, it is possible to easily estimate the shape of the distal surface of the implant.

Examples of such a bone include a cranium bone, a facial bone or a maxillofacial bone and the like. The following description will be made with regard to an example where the implant of the present invention is applied to a cranium bone.

<Creation of Three-Dimensional Image Data of Bone>

First, as shown in FIG. 1, three-dimensional data 10 of a bone having a defect is created. The three-dimensional data 10 of the bone is created based on a plurality of tomgraphic image data.

In the present invention, as for such tomographic image data, tomographic image data obtained based on measurement data by MRI (magnetic resonance imaging) is employed.

The measurement of MRI is performed utilizing a magnetic resonance phenomenon. In the case of CT scanning, exposure to X-ray radiations can not be avoided when measurement is carried out. On the other hand, in the case of MRI, there is no exposure to X-ray radiations. That is, in the case of MRI, since it is not necessary to consider a risk of exposure to X-ray radiations, many tomographic image data and more detailed tomographic image data can be obtained from a bone to which an implant is applied. As a result, a manufactured implant will have excellent shape-conformability to the defect of the bone.

In the meantime, there is a case that the shape of a defect of a bone changes with the elapse of time due to bone formation (osteogenesis) or the like. Therefore, in order to obtain an implant having more excellent shape-conformability, it is necessary to shorten a time period from a point of time that measurement for obtaining the tomographic image data of a bone is carried out to a point of time that bone defect reconstruction is carried out. In this regard, MRI does not use X-ray, it is not necessary to consider a risk caused by exposure to X-ray radiations even if measurement is carried out repeatedly. Therefore, by carrying out measurement of MRI for several times, it is possible to utilize the newest tomographic image data to the modeling of an implant without accompanying any disadvantage such as exposure to X-ray radiations. As a result, it becomes possible to obtain an implant having excellent shape-conformability.

Further, when CT is used to obtain tomographic images of a bone, there is a case that a patient must take a forced posture upon measurement depending on a region of a defect of a bone. This imposes larger burden to the patient. However, in the case of MRI, it is possible to obtain tomographic image data along arbitral cross sections without changing a posture of a patient, the burden to the patient can be released or reduced.

The method for obtaining a plurality of tomographic image data is not limited to a specific method, but the following method is preferable. Namely, first, by inverting a threshold value of measurement data of MRI to obtain threshold value inverting data and then a bone region is extracted from the threshold value inverting data. This is because of the following reason.

A bone (bone tissue) is mainly formed of phosphate such as calcium phosphate, so that the content of hydrogen atoms is low as compared with other tissues (e.g. muscular tissue, connective tissue, epithelial tissue and the like). Usually, measurement of MRI is carried out by detecting hydrogen atoms ($^1$H). Therefore, in the measurement data of MRI directly obtained by MRI scanning, an image of a bone itself does not appear in a substantially visible manner. For this reason, in the conventional method for modeling an implant, measurement data of MRI has not been used, while measurement data of CT has been used since a bone itself can be clearly visualized based on the measurement data thereof. However, in a preferred embodiment of the present invention measurement data of MRI is used, in which the threshold value of the measurement data of MRI is inverted to obtain threshold value inverting data as described above. Based on the thus obtained threshold value inverting data, a bone region can be clearly imaged, thereby enabling to extract only data of a region of a bone (that is, tomographic image data of a bone) easily.

In this regard, it is to be noted that the measurement data of MRI is not limited to one obtained by a magnetic resonance phenomenon of hydrogen atoms ($^1$H). For example, the MRI image data may be one obtained by a magnetic resonance phenomenon of a nuclide other than hydrogen atoms ($^1$H) such as $^{31}$P. In a living body, P (phosphorous) is unevenly distributed in a bone tissue particularly. Therefore, if a probe of MRI that is capable of detecting $^{31}$P is used, clear image data of a bone itself can be obtained in the form of MRI image data. With this result, it becomes possible to obtain tomographic image data of a bone without performing a process for inverting a threshold value of MRI measurement data.

By stacking thus obtained plural tomographic data, it is possible to produce three-dimensional image data 10.

The slice interval of the tomographic data (the distance between the adjacent tomographic images or scanning planes) is not limited to a specific value, but 0.1–5 mm is preferable, and 0.3–3 mm is more preferable.

If the slice interval is less than the lower limit value, the number of required tomographic images becomes too many depending on the size of the implant. As, a result, a time required for producing the three-dimensional image data 10 becomes long and further improvement of quality of image of the three-dimensional image data 100 can not be expected, so that there is a case that it becomes impossible to further improve dimensional accuracy of an implant to be manufactured.

On the other hand, if the slice interval exceeds the upper limit value, there is a possibility that quality of the three-dimensional image data becomes insufficient.

Further, it is preferred that the three-dimensional image data 10 is obtained by carrying out a smoothing treatment on the outer surface after stacking a plurality of tomographic image data. By doing such a treatment, a manufactured implant can have especially excellent shape-conformability with a defect of a bone.

Based on the three-dimensional image data thus obtained, a shape of a missing bone that was previously present or should have been present in the defect 101 is estimated, and a shape of such a missing bone is obtained in the form of three-dimensional image data (missing bone data 13). Based on the missing bone data, three-dimensional data of an implant is produced.

The missing bone data 13 can be obtained by the following method.

<Estimate of a Shape of a Distal Surface of a Missing Bone That Should Have Been Present in the Defect of the Bone>

To obtain the missing bone data 13, distal surface contour data 131 of a missing bone that should have been present in the defect 101 is first produced based on the three-dimensional image data obtained as described above.

As for the distal surface contour data 131, contour data of the distal surface of a missing bone to be present in the defect 101 (which can be obtained from the three-dimensional image data 10) may be used as it is. However, when the three-dimensional image data 10 is obtained from a bone having plane symmetry, it is preferred that the distal surface contour data is obtained in the following manner.

First, two divided bodies that could be obtained when the three-dimensional data 10 is divided along the symmetry plane 102, that is a divided body 11 which has the defect 101 and a divided body 12 which does not have the defect 101 are assumed.

Next, at least a part of the distal surface shape data of the divided body 12 is transferred to the side of the divided body 11 in an inverting manner. In this case, it is necessary that the distal surface shape data of the divided body 12 to be transferred includes at least shape data of a symmetrical non-defect part 103 which is a part of the divided body 12 symmetrical to the defect 101.

When the distal surface shape data of the divided body 12 is transferred in this way, a portion where both the shape data are overlapped represents a non-defect part 105 of the divided body 11 Therefore, by extracting data of a part which does not overlap with the distal surface shape data of the divided body 11, it is possible to determine a distal surface shape (distal surface shape data 132) of an implant to be applied to the defect 101 (see FIG. 2). A contour of periphery of thus obtained distal surface shape data 132 is used for contour data 131 of the missing bone data 13.

By obtaining the contour data 131 in this way, even when a shape of a contour of periphery of the inclined surfaces of the side walls 104 of the defect is not known, it is possible to obtain sufficiently accurate contour data 131.

Further, when using such a method, it is possible to obtain shape data of the entire of the distal surface of the missing bone to be present in the defect 101 (that is, distal surface shape data 132), in addition to the contour data 131. By obtaining the distal surface shape data 132 in this way, it becomes possible to estimate a complicated shape of a bone such as fine regularities inherently formed with the bone. With this result, a manufactured implant can have especially excellent shape-conformability with the defect of the bone.

Further, in the method mentioned above, since the distal surface shape of the missing bone to be present in the defect 101 is estimated using the shape data of other part of the bone (that is, the distal surface shape data of the symmetrical non-defect part 103), it is possible to manufacture an implant having excellent shape-conformability with the defect of the bone even if the implant to be manufactured has a relatively large size.

Furthermore, it is preferred that the distal surface shape data 132 thus estimated forms a continuous surface with the distal surface of the three-dimensional image data 10. This makes it possible for the manufactured implant to have especially excellent shape-conformability with the defect the bone.

In the above embodiment, the contour data 131 and the distal surface shape data 132 are obtained simultaneously. However, these data may be obtained separately. For example, the distal surface shape data 132 may be determined after obtaining the contour data 131.

<Estimation for the Thickness of the Implant>

The shape of the implant having a predetermined thickness is estimated using the distal surface shape data 132 that is estimated in the manner described above, and thereby obtaining data of a provisional shape of an implant from which the missing bone data 13 is obtained.

Usually, the thickness of the implant is estimated based on the thickness of the bone at the non-defect part 105.

When the thickness of the implant is estimated in this manner, the contour of the outer periphery of the implant usually has substantially the same shape along its thickness direction. In other words, the outer peripheral surface of the provisional shape of the implant (that is, the outer peripheral surface to be in contact with the side walls 104) has a smooth shape in the thickness direction having substantially no regularities.

In this regard, it is to be noted that the provisional shape data of the implant may be in the form of any three-dimensional data represented by dots, lines or planes.

<Estimation (Correction) for the Shape of the Outer Peripheral Surface to be in Contact with the Side Walls>

In the meantime, the side walls of the defect of the bone usually have fine irregularities. Namely, the side walls do not have a constant shape in the thickness direction of the bone. In many cases, the area of the distal surface side of the defect tends to be larger than the area of the proximal surface side thereof. This is because a defect of a bone has been normally processed into a shape by which an implant does not fall into the inside of a cranium bone before the implant is applied to the defect.

Therefore, the provisional shape data of the implant obtained in the manner described above necessarily contains overlapping portions which overlap with the non-defect part 105 of the three-dimensional image data 10 when the provisional shape data of the implant is superposed on the defect 101 in the three-dimensional image data 10. These overlapping portions are shown in FIG. 3 as triangular shapes with hatchings. If such overlapping portions are left as they are, a manufactured implant will not be conformable with the side walls of the defect when it is applied to the defect of the bone.

Therefore, in the present invention, the provisional shape data of the implant is corrected so as to be conformable with the shape of the side walls 104 when the provisional shape data of the implant is superposed on the defect 101 in the three-dimensional image data 10, thereby obtaining the missing bone data 13. Namely, one of the features of the present invention resides in that an implant is modeled so that a finally manufactured implant can have good conformability with the side walls of the defect of the bone.

Such correction is carried out for example by deleting the data of the overlapping portions 133 where the provisional shape data of the implant overlaps with the non-defect part 105 from the provisional shape data of the implant in the state that the distal surface shape data 132 is in conformity with the contour of the defect at the distal surface side thereof (see FIG. 4). The provisional shape data of the implant which has been corrected in this way is used as the missing bone data 13, and based on the missing bone data 13, three-dimensional data of an implant is obtained.

An implant manufactured based on the three-dimensional data of the implant will have excellent conformability with the shape of the side walls of the defect of the bone. As a result, the manufactured implant will have excellent stability when it is applied to the bone.

Further, in the present invention, since an implant is modeled so that it will be conformable with the shape of the side walls of the defect of the bone, a trimming process for the implant, which has been carried out during surgical operation in the conventional method, can be omitted or simplified. As a result, it is possible to shorten a time required for the operation, thereby enabling to reduce the burden to a patient.

The missing bone data 13 obtained in the manner described above can be used as shape data (that is, the three-dimensional data of the implant) for manufacturing an implant as it is, or further corrections may be made thereto, if necessary. Examples of such corrections to the missing bone data 13 include changes in curvature or thickness for at least a part thereof. By making such corrections, a finally manufactured implant will have especially excellent shape-conformability with a bone. Further, an implant modeled according to the method of the present invention may have a mirror image relationship with respect to the symmetrical non-defect part 103, or may not have such a relationship.

The missing bone data 13 obtained in the manner described above is acceptable if at least a part of the periphery thereof is conformable with the shape of the side walls 104 of the defect in the three-dimensional image data. However, it is preferred that the missing bone data 13 conforms with the shape of the side walls of the defect in the three-dimensional image data 10 through the entire of the outer periphery thereof. In the latter case, a finally manufactured implant will have a further improved stability when applied to a defect of a bone.

<Manufacture of the Implant>

Next, a description will be made with regard to the implant of the present invention. The implant of the present invention is manufactured based on the modeling method described above. In this regard, it is to be noted that, when manufacturing an implant, various treatments such as rotation and the like may be made to the finally obtained missing bone data 13 (to which the correction has been already carried out) which is obtained by the method described above.

Hereinbelow, a description will be made with regard to a method for manufacturing an implant based on a preferred embodiment shown in the accompanying drawings.

Figure 5:
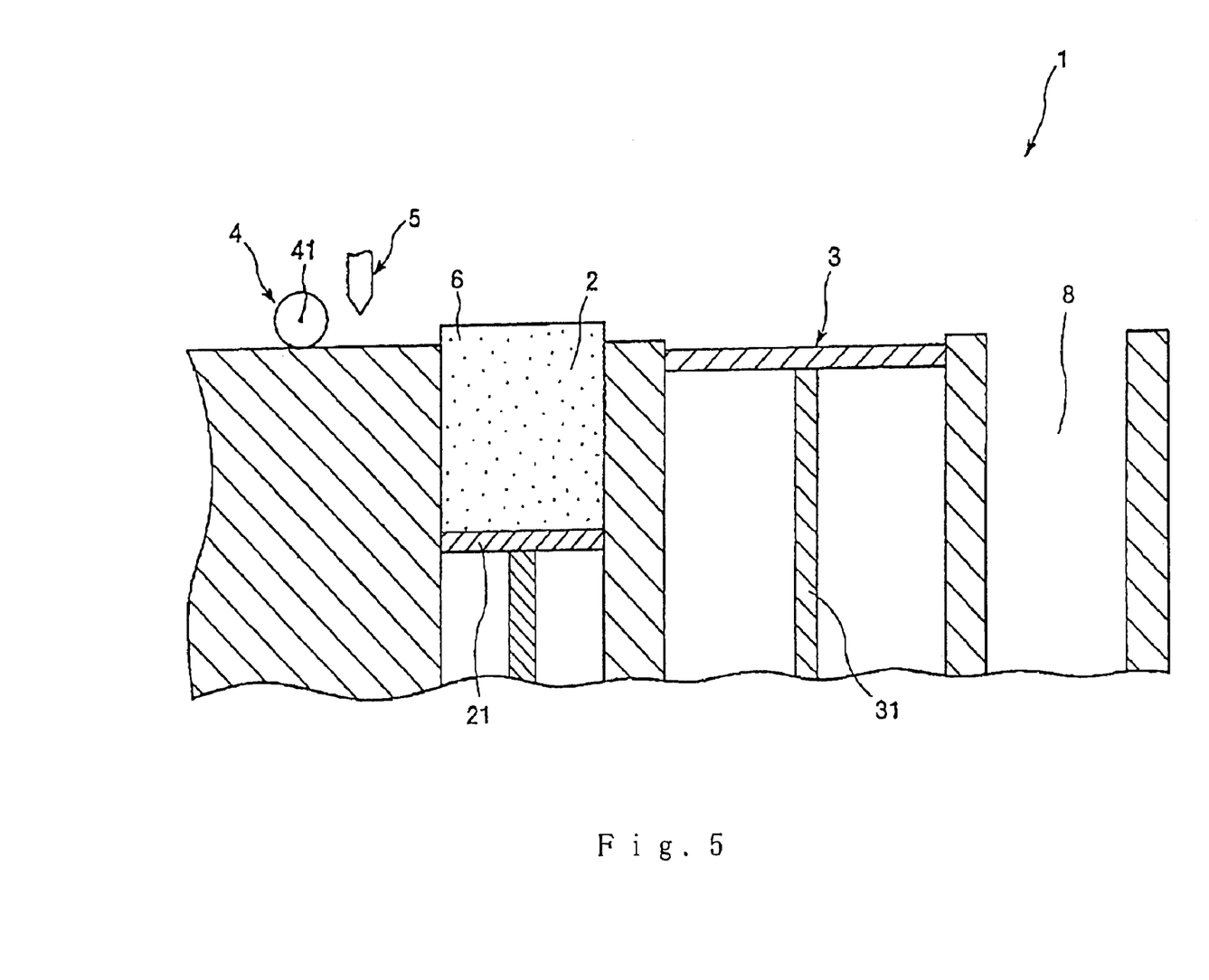
FIG. 5 shows the structure of a manufacturing apparatus used in a preferred embodiment of the method for manufacturing an implant.
Figure 6:
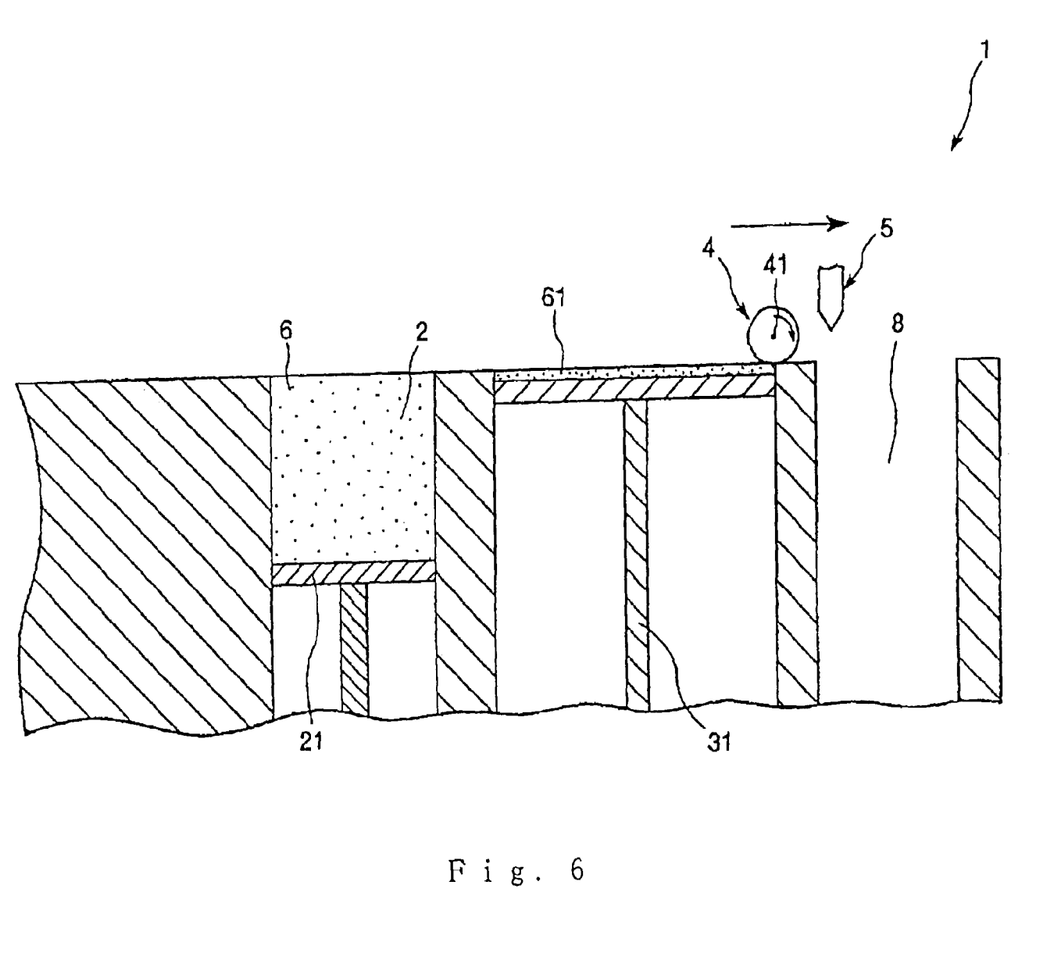
FIG. 6 shows a first step of the manufacturing method of the implant.
Figure 7:
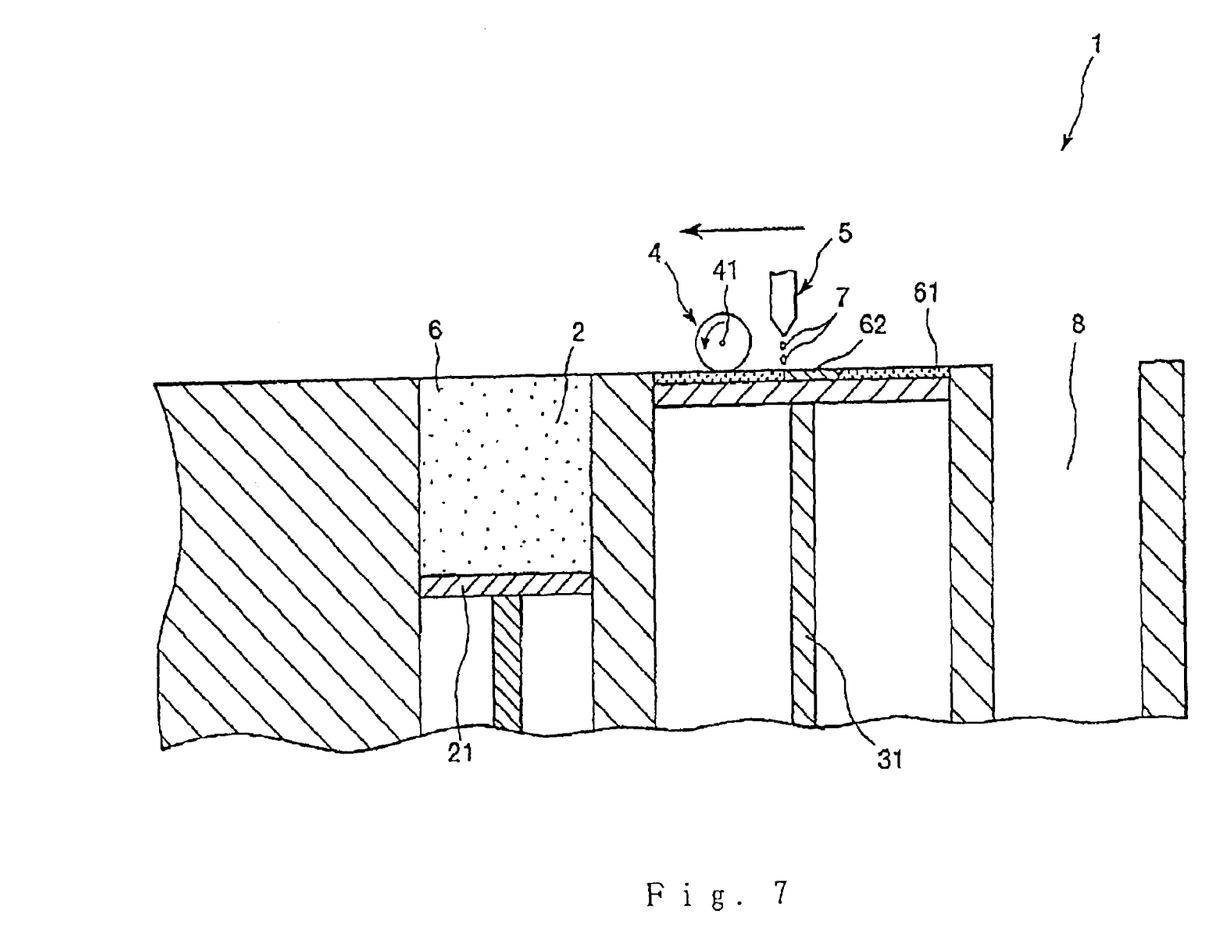
FIG. 7 shows a second step of the manufacturing method of the implant.
Figure 8:
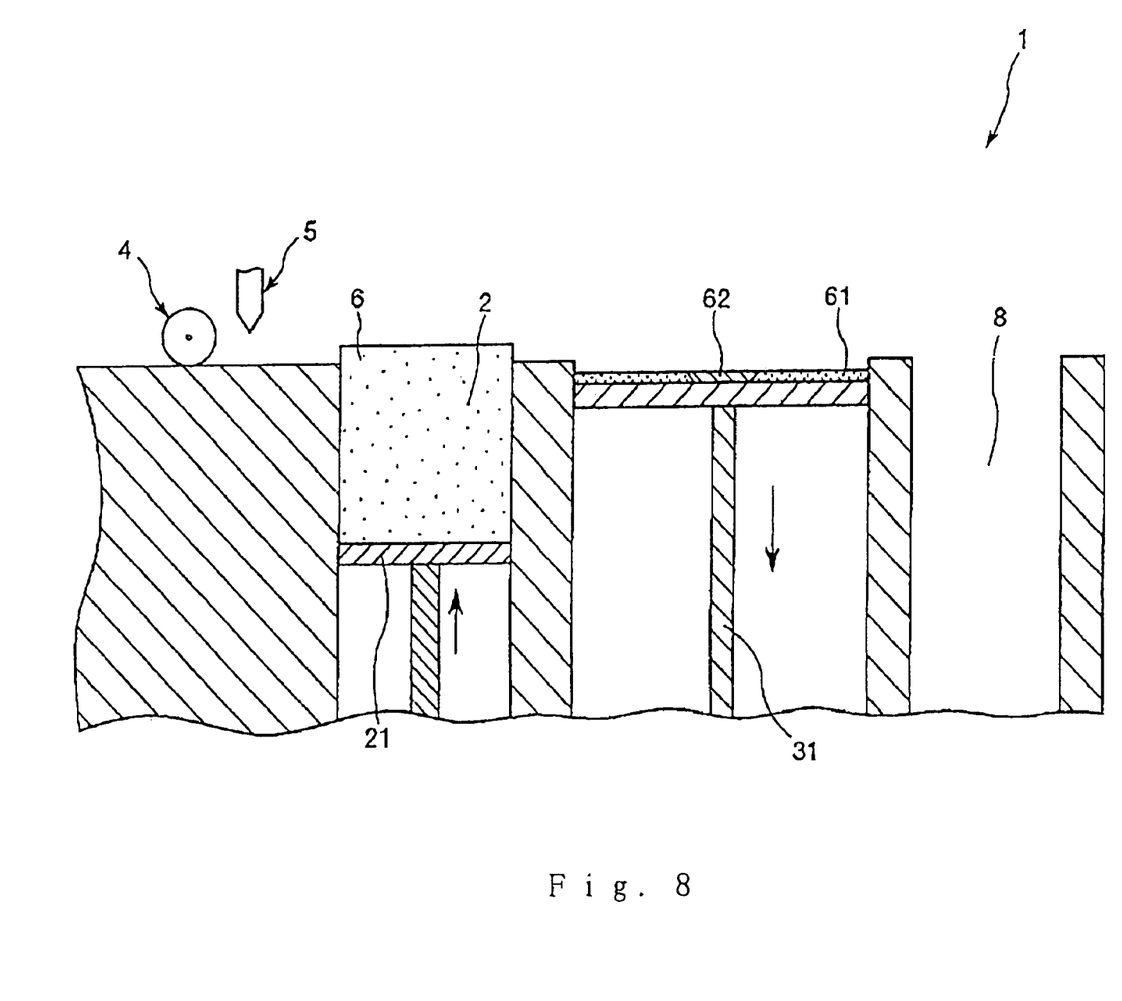
FIG. 8 shows a third step of the manufacturing method of the implant.
Figure 9:
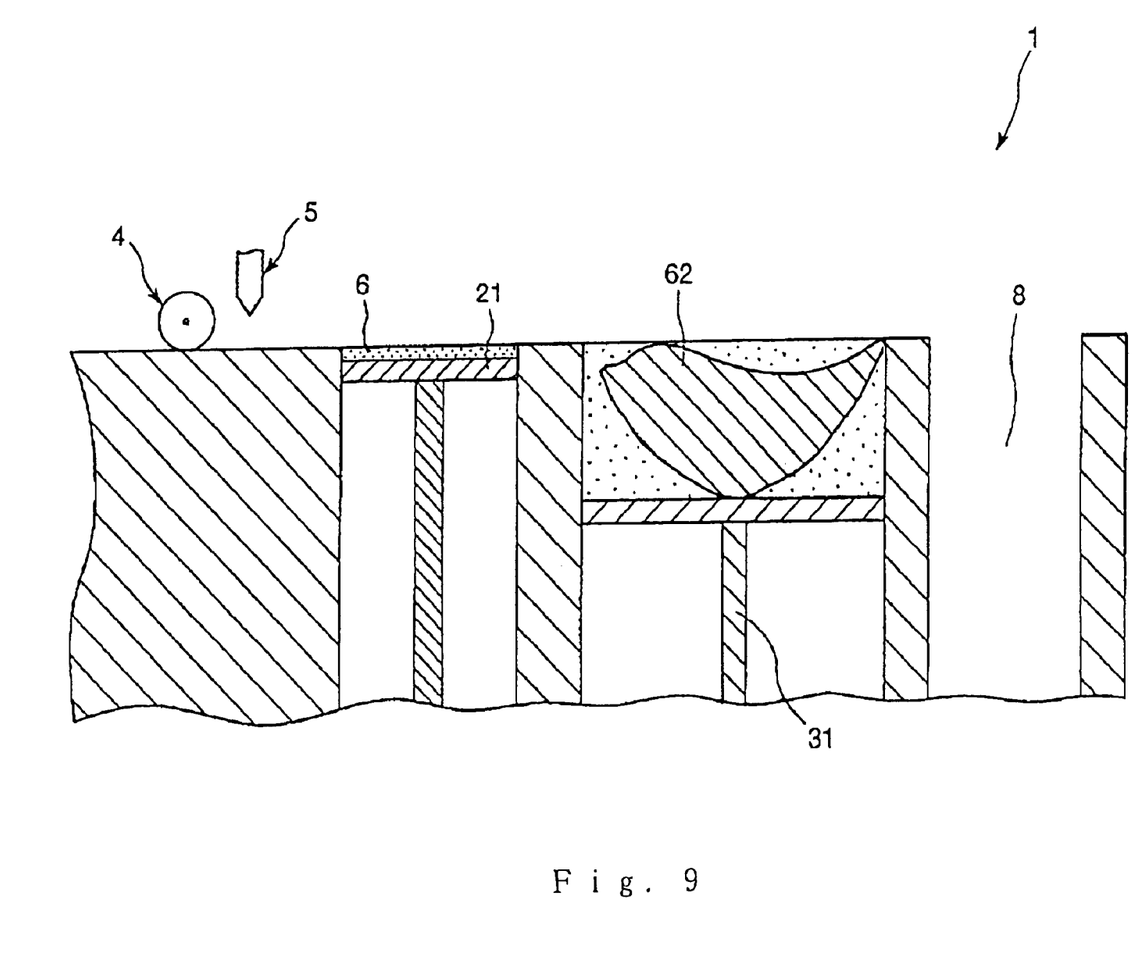
FIG. 9 shows a state that the first to third steps shown in FIGS. 6 to 8 have been repeatedly carried out.
Figure 10:
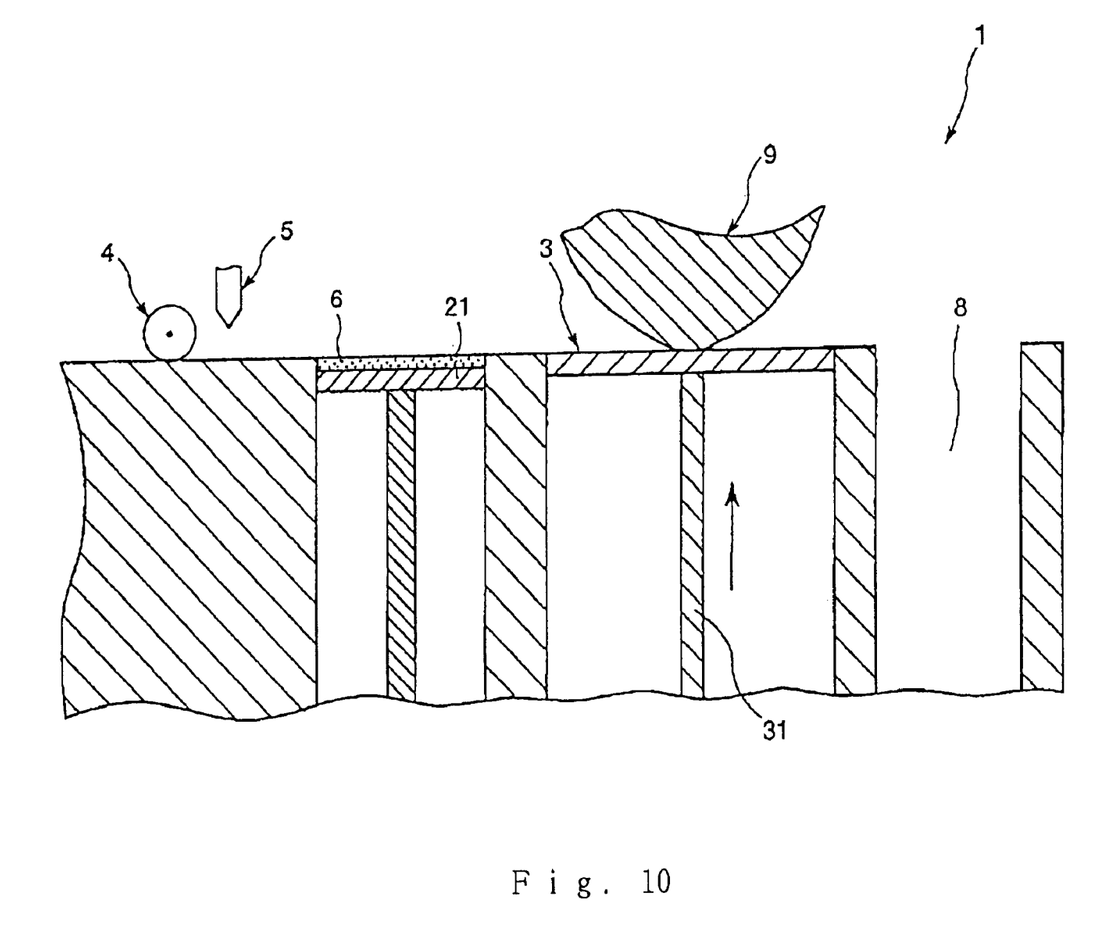
FIG. 10 shows the shape of an implant obtained by carrying out the first to third steps shown in FIGS. 6 to 8 repeatedly.

FIG. 5 shows the structure of a manufacturing apparatus used in a preferred embodiment of the method for manufacturing an implant, FIG. 6 shows a first step of the manufacturing method of the implant, FIG. 7 shows a second step of the manufacturing method of the implant, FIG. 8 shows a third step of the manufacturing method of the implant, FIG. 9 shows a state that the first to third steps shown in FIGS. 6 to 8 have been repeatedly carried out, FIG. 10 shows the shape of an implant obtained by carrying out the first to third steps shown in FIGS. 6 to 8 repeatedly.

The implant 9 of the present invention can be manufactured using the manufacturing apparatus shown in FIG. 5, for example.

As shown in FIG. 5, generally, the implant manufacturing apparatus 1 includes a material powder supply section (tank) 2, an implant forming stage 3, a roller 4 and a liquid supply head 5.

In the material powder supply section 2, a material powder 6 used for manufacturing the implant 9 is stored.

A bottom portion 21 of the material powder supply section 2 is constructed from a piston which is movable in the vertical direction.

The implant forming stage 3 is a stage on which the material powder 6 supplied from the material powder supply section 2 is reacted with a reaction liquid 7 to manufacture the implant 9.

The implant forming stage 3 is also constructed so as to be movable in the vertical direction.

The roller 4 rotates about an axis 41 to move over the material powder supply section 2 and the implant forming stage 3 substantially in the horizontal direction. The roller 4 has a function of forming a layer 61 on the implant forming stage 3 using the material powder from the material powder supply section 2.

The liquid supply head 5 has a function of dispensing the reaction liquid 7 toward at least a part of the layer 61 formed of the material powder 6.

In this regard, it is to be noted that each of the material powder supply section 2, the implant forming stage 3 and the roller 4 has a predetermined length along the depth direction, that is the direction perpendicular to the sheet of FIG. 5. Further, the liquid supply head 5 moves in the horizontal direction together with the roller 4, and it can also move along the depth direction while moving in the horizontal direction.

Hereinbelow, a description will be made with regard to each of the steps of the manufacturing method using the implant manufacturing apparatus 1.

(1) Forming a Layer Made of the Material Power (First Step)

First, using the material powder in the material powder supply section 2, the layer 61 made of the material powder 61 is formed on the implant forming stage 3.

As shown in FIG. 6, in this embodiment, when the roller 4 moves over the material powder supply section 2 and the implant forming stage 3 in the horizontal direction with being rotated about the axis 41, the material powder at the vicinity of the upper surface of the material powder supply section 2 is supplied onto the implant forming stage 3 to form the layer 61.

There is no specific limitation to the average thickness of thus formed layer 61, but preferably the average thickness is in the range of 0.1 mm to 0.5 mm, and more preferably in the range of 0.1 to 0.3 mm.

If the average thickness of the layer 61 is less than the lower limit value, there is tendency that the layer 61 has uneven thicknesses at various portions thereof. Further, depending on the size of the implant to be manufactured, it takes a long time to manufacture the implant, thus resulting in the lowered productivity.

On the other hand, if the average thickness of the layer 61 exceeds the above upper limit value, the reaction liquid 7 will not be reacted sufficiently, so that there is a possibility that the mechanical strength of the obtained implant 9 becomes insufficient. Further, there is tendency that the dimensional precision of the manufactured implant 9 becomes lowered.

The remaining part of the material powder 6 that has been supplied from the material powder supply section 2 is collected to a material powder collecting section (tank) 8.

(2) Dispensing the Reaction Liquid (Second Step)

Next, at least a part of the layer 61 formed in a manner described above is made contact with the reaction liquid 7. The reaction liquid 7 is dispensed onto the layer 61 at various points by moving the liquid supply head 5 along not only the horizontal direction but also the depth direction.

With this result, chemical reaction is developed between the reaction liquid 7 and the material powder 6 forming the layer 61. Due to the chemical reaction, the material powder 6 is hardened to form a hardening portion 62.

In this way, it is possible to harden the material powder 6 without adding any binder. Accordingly, it is possible to obtain an implant 9 having a high purity containing less impurities. As a result, the obtained implant 9 can have especially excellent biocompatibility. The details of the material powder 6 and the reaction liquid 7 will be described later.

In this embodiment, the reaction liquid is dispensed from the liquid supply head 5 as droplets. By supplying the reaction liquid as droplets, the material powder 6 can be made contact with the reaction liquid accurately and efficiently at a target position. As a result, the dimensional accuracy of the obtained implant 9 becomes further excellent, and the productivity can also be improved.

As shown in FIG. 7, in this step, the liquid supply head 5 moves above the material powder supply section 2 and the implant forming stage 3 sequentially in the horizontal direction to dispense the reaction liquid 7 as droplets so that the hardening portion 62 has a target pattern. The dispensing pattern of the reaction liquid 7 is determined based on the three-dimensional pattern of the implant obtained by the implant modeling method described above. Further, if the hardening portion 62 will be shrunk in the later step, the dispensing patter is determined by taking the possible shrinkage into account.

(3) Third Step

Then, by moving the bottom 21 of the material powder supply section 2 upwardly, the height of the upper surface of the material powder 6 in the material powder supply section 2 is adjusted. Further, by moving the implant forming stage 3 downwardly, the height of the upper surface of the layer 61 is adjusted.

In this case, it is preferred that the moving distance of the bottom 21 is substantially the same as the height of the material powder that has been supplied from the material powder supply section 2 in the first step. Further, it is also preferred that the moving distance of the implant forming stage 3 is substantially the same as the average thickness of the layer 61 formed in the first step. This makes it possible to keep the thickness of each of the stacked layers 62 constant.

Thereafter, by repeating the first, second and third steps, a number of layers 61 are stacked as shown in FIG. 9 so that an implant having a shape corresponding to the three-dimensional pattern obtained by the modeling method described above is formed from the hardening portions 62.

As described above, in this embodiment, an implant 9 having the target shape is manufactured by stacking hardening portions 62. Therefore, even in the case where the target implant 9 has a complicated shape. It is possible to manufacture it easily. Further, it is also possible to obtain an implant 9 having excellent dimensional accuracy. Furthermore, since a target implant 9 can be manufactured in a relatively short period of time, this can be used for emergency operation or the like.

Thereafter, as shown in FIG. 10, the implant forming stage 3 is moved upwardly to remove the unhardened material powder, thereby enabling to obtain a three-dimensional implant 9 having the target shape. Such unhardened material powder 6 can be removed by blowing air thereto, for example.

If necessary, other treatments such as sintering or impregnation of drugs (e.g. bone formation factor such as BMP, TGF, bone inducing factor such as PG) may be carried out as pre-treatment, intermediate treatment or post-treatment.

It is preferred that thus obtained implant 9 has an adequate porosity. If the implant has such a porosity, osteoblast will easily enter the pores of the implant 9 when the implant 9 is implanted into a living body so that bone formation progresses smoothly. As a result, it is possible to shorten a time required until the implant will exhibit an stable effect. The porosity of the implant 9 is preferably in the range of 10 to 90 vol %, and more preferably:in the range of 30 to 80 vol %.

Further, it is also preferred that the pores formed in the implant 9 are continued with each other and the average pore size thereof is greater than 100 μm. If the average pore size is less than 100 μm, osteoblast will be hard to enter the pores in the implant 9, so that there is a possibility that bone formation will not be difficult to progress.

On the other hand, if the porosity of the implant 9 exceeds the above upper limit value, there is a possibility that the implant 9 can not have sufficient mechanical strength.

As described above, in this embodiment, the material powder 6 is hardened by the reaction between the material powder 6 and the reaction liquid 7. This means that it is possible to harden the material powder 6 without adding any binder. Therefore, the obtained implant 9 contains less impurities to have high purity. With this result, the obtained implant 9 has especially excellent biocompatibility.

Further, of course, the material powder 6 and the reaction liquid 7 also have excellent biocompatibility. Therefore, eve in the case where unreacted material powder and/or reaction liquid remain in the implant due to some reasons, it is possible to suppress that any adverse effect will arise in a living body.

Hereinbelow, a description will be made with regard to the material powder 6 and the reaction liquid 7 in more details.

<Material Powder>

In this embodiment, as for the material powder, powder containing α-tricalcium phosphate (α-TCP), tetracalcium phosphate (TeCP) and calcium hydrogen phosphate may be used, for example.

The α-tricalcium phosphate (α-TCP) and tetracalcium phosphate (TeCP) may be those produced by the know methods, respectively. Alternatively, mixture of α-tricalcium phosphate and tetracalcium phosphate which is obtained by sintering hydroxyapatite may be used for the powder.

When sintering hydroxyapatite, the sintering may be carried out under reduced pressure at a temperature of 1150° C. to 1450° C. for about one hour, for example Further, as for the calcium hydrogen phosphate, it may be produced by any one of the known methods, and either of anhydrate ($CaHPO_4$) or hydrate (e.g. dihydrate such as $CaHPO_4.2H_2O$ and the like) may be used.

If necessary, the material powder may further, contain hydroxyapatite, fluorine apatite, β-tricalclum phosphate, calcium pyrophosphate and the like in addition to the above described three components.

The material powder 6 is chemically reacted when it is made contact with the reaction liquid described later to be hardened.

Further, the Ca/P ratio of the material powder 6 is preferably in the range of 1.40 to 1.80, and more preferably in the range of 1.40 to 1.67. If the Ca/P ratio is less than 1.40 or more than 1.80, there is a case that the reaction speed when hardening is lowered, or the mechanical strength of the obtained implant 9 is lowered.

Furthermore, if necessary, the material powder 6 may further contain as additives bone formation factor such as BMP and TGF, bone inducing factor such as PG, and/or antibacterial agent. Examples of antibacterial agent include iodoform, chlorhexidine and the like.

The average particle size of the material powder 6 is preferably in the range of 10 to 100 μm, and more preferably in the range of 20 to 40 μm.

If the average particle size of the material powder 6 is smaller than the lower limit value, it becomes difficult to handle the material powder 6. Further, if the average particle size of the material powder 6 is smaller than the lower limit value, the porosity of the obtained implant 9 becomes too low, thus resulting in the case that bone formation will be difficult to progress.

On the other hand, if the average particle size of the material powder 6 exceeds the above upper limit value, there is a case that sufficient dimensional accuracy will not be obtained depending on the size of an implant 9 to be manufactured.

<Reaction Liquid>

As for the reaction liquid 7, various types may be used if they can be reacted with the material powder 6 so that the material powder 6 is hardened, but water or one containing water as a major component thereof is preferable.

By using such a reaction liquid, a hardening portion 62 which is formed by the reaction of the material powder 6 with the reaction liquid 7 can have especially excellent mechanical strength. Further, when water or one containing water as a major component thereof is used as the reaction liquid 7, an apatite (such as hydroxyapatite or octacalcium phosphate) will be produced, and such an apatite has especially excellent biocompatibility. As a result, it is possible to provide an implant 9 having high safety.

The reaction liquid 7 may further contain as constituents other than water. Example of such additional constituents include organic acids such as acetic acid, lactic acid, citric acid, malic acid, malonic acid, succinic acid, glutaric acid, tartaric acid, polyacrylic acid, gluconic acid; inorganic acids such as phosphoric acid; pH adjusting agent; thickener: X-ray contrast agent; antibacterial agent; bone formation factor such as BMP and TGF; bone inducing factor such as PG; and the like.

Further, the reaction liquid 7 may contain any insoluble constituents if the reaction liquid 7 still has sufficient fluidity.

In the foregoing, the method for manufacturing an implant and the implant manufactured by the method according to the present invention have been described, but the present invention is not limited thereto.

For example, the above description of the embodiment has been directed to the case where the implant is applied to a cranium bone. However, the present invention is not limited thereto, and the present invention may be applied to various bones other than the cranium bone.

Further, in the above embodiment, the reaction liquid is described as being the type that can be chemically reacted with the material powder to harden the material powder, but the reaction liquid of the present invention is not limited to such a type. Namely, various types of reaction liquids may be used if they can harden the material powder. For example, a liquid containing methylcellulose or polyvinyl alcohol which can harden the material powder without chemical reaction may be used (namely, a binder type reaction liquid may be used).

As described above, according to the present invention, it is possible to provide an implant having excellent shape-conformability with a defect of a bone.

In particular, since the present invention utilizes tomographic image data of the a bone obtained from measurement data of MRI for forming three-dimensional image of the bone, it is possible to provide an implant having excellent shape-conformability with a defect of a bone without giving an adverse effect such as exposure to X-ray irradiations to a patient.

Further, in the present invention, even if an implant has a relatively large size, it is possible to provide an implant having excellent shape-conformability with a defect of a bone.

Furthermore, in the present invention, it is possible to omit or simplify a trimming treatment which is carried out upon operation in the conventional method. As a result, a time required for operation can be shortened, thus resulting in reduced burden to a patient.

Moreover, according to the present invention, it is also possible to form an implant having excellent shape-conformability with a defect of a bone which can be used for other bones such as a facial bone or a maxillofacial bone for which it were difficult to estimate a shape of a missing bone to be present in a defect of the bone by the conventional method.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2002-218153 (filed on Jul. 26, 2002) which is expressly incorporated herein by reference in its entireties.

What is claimed is:

1. A method for modeling an implant to be applied to a defect of a bone, the defect having side walls, comprising:
   obtaining a plurality of tomographic image data of the bone based on magnetic resonance imaging (MRI) measurement data, the tomographic image data being obtained by inverting a threshold value of the MRI measurement data to obtain threshold value inverting data, and extracting a bone region from the threshold value inverting data;
   producing three-dimensional image data of the bone based on the plurality of tomographic image data; and
   estimating a shape of a missing bone that was previously present or should have been present in the defect of the bone to obtain three-dimensional data of the implant, wherein the three-dimensional data of the implant is modeled such that at least a part of an outer periphery of the implant is conformable with a shape of the side walls of the defect of the bone.

2. The method as claimed in claim 1, wherein estimating comprises:
   estimating a provisional shape of the implant which has a contour conformable with the shape of a contour of a periphery of the side walls of the defect at a distal surface of the bone and has a predetermined thickness; and
   deleting data of portions of the provisional shape of the implant that overlap the bone from the data of the provisional shape of the implant so that the three-dimensional data of the implant has an outer peripheral shape that is conformable with the shape of the side walls of the defect.

3. An implant which is manufactured based on a model prepared in accordance with the modeling method as defined in claim 2.

4. The method as claimed in claim 1, wherein estimating comprises:
   producing data of a contour of a distal surface of the implant so that the contour is conformable with the shape of a contour of a periphery of the side walls at a distal surface of the bone;
   estimating a provisional shape of the implant which has a predetermined thickness and has a substantially predetermined shape in the thickness direction thereof using the data of the contour of the distal surface of the implant; and
   deleting data of portions of the provisional shape that overlap the bone from the data of the provisional shape of the implant so that the three-dimensional data of the implant has an outer peripheral shape that is conformable with the shape of the side walls of the defect.

5. An implant which is manufactured based on a model prepared in accordance with the modeling method as defined in claim 4.

6. The method as claimed in claim 1, wherein the estimating comprises:
producing data of a contour of a distal surface of the implant so that the contour is conformable with the shape of a contour of a periphery of the side walls at a distal surface of the bone;
estimating a provisional shape of the implant which has a predetermined thickness and has a substantially predetermined shape in the thickness direction thereof using the data of the contour of the distal surface of the implant; and
correcting the data of the provisional shape so that the three-dimensional data of the implant has an outer peripheral shape that is conformable with the shape of the side walls of the defect by comparing the estimated data of the provisional shape of the implant with the data of the side walls of the three-dimensional image data.

7. An implant which is manufactured based on a model prepared in accordance with the modeling method as defined in claim 6.

8. The method as claimed in claim 1, wherein when the implant is applied to the defect of the bone, and a distal surface of the implant forms a continuous surface with the distal surface of the bone.

9. An implant which is manufactured based on a model prepared in accordance with the modeling method as defined in claim 8.

10. The method as claimed in claim 1, wherein the bone substantially has plane symmetry, in which the estimation of the shape of the missing bone is carried out by utilizing data of a portion of the three-dimensional image data which is plane-symmetrical with the defect in the three-dimensional image data.

11. An implant which is manufactured based on a model prepared in accordance with the modeling method as defined in claim 10.

12. The method as claimed in claim 1, wherein the bone is a cranium bone.

13. An implant which is manufactured based on a model prepared in accordance with the modeling method as defined in claim 12.

14. The method as claimed in claim 1, wherein the plurality of tomographic images for producing the three-dimensional image data are taken with a predetermined slice interval between the adjacent images, in which the slice interval is in the range of 0.1 to 5 mm.

15. An implant which is manufactured based on a model prepared in accordance with the modeling method as defined in claim 14.

16. An implant which is manufactured based on a model prepared in accordance with the modeling method as defined in claim 1.

17. The implant as claimed in claim 16, wherein the implant is manufactured through a manufacturing process which comprises:
forming a layer made of material powder; and
hardening the material powder by making at least a part of the layer contact with a reaction liquid,
wherein the forming and hardening are carried out repeatedly to obtain a laminate comprised of a plurality of layers, thereby manufacturing an implant having a shape corresponding to the three-dimensional data of the implant provided by the modeling method.

18. The implant as claimed in claim 16, wherein the implant has a porosity of 10 to 90 vol %.

* * * * *